(12) United States Patent
 Cardinault

(10) Patent No.: US 10,463,700 B2
(45) Date of Patent: Nov. 5, 2019

(54) USE OF PROPOLIS FOR COMBATING THE SIDE EFFECTS OF CHEMOTHERAPY

(71) Applicant: POLLENERGIE, Saint-Hilaire-de-Lusignan (FR)

(72) Inventor: Nicolas Cardinault, Agen (FR)

(73) Assignee: POLLENERGIE, Saint Hilaire de Lusignan (FR)

( * ) Notice: Subject to any disclaimer, the term of this patent is extended or adjusted under 35 U.S.C. 154(b) by 361 days.

(21) Appl. No.: 14/898,024

(22) PCT Filed: Jun. 11, 2014

(86) PCT No.: PCT/FR2014/051407
 § 371 (c)(1),
 (2) Date: Dec. 11, 2015

(87) PCT Pub. No.: WO2014/199076
 PCT Pub. Date: Dec. 18, 2014

(65) Prior Publication Data
 US 2016/0129052 A1    May 12, 2016

(30) Foreign Application Priority Data

Jun. 11, 2013 (FR) ...................................... 13 55356

(51) Int. Cl.
 *A61K 35/644* (2015.01)
 *A23L 33/10* (2016.01)
 *A23L 21/20* (2016.01)

(52) U.S. Cl.
 CPC ............ *A61K 35/644* (2013.01); *A23L 21/20* (2016.08); *A23L 33/10* (2016.08); *A23V 2002/00* (2013.01)

(58) Field of Classification Search
 None
 See application file for complete search history.

(56) References Cited

PUBLICATIONS

Oršolić, et al., Biomedicine & Pharmacotherapy, 59:561 (Year: 2005).*
Kumazawa, et al., Food Chemistry, 84:329 (Year: 2004).*
U.S. Appl. No. 14/534,950, filed Jun. 2017, Cardinault; Nicolas.*
Oršolić, et al., Med. Oncol., 27:1346. (Year: 2010).*

* cited by examiner

*Primary Examiner* — Michael Barker
(74) *Attorney, Agent, or Firm* — Young & Thompson

(57) ABSTRACT

The use of a composition including at least one extract of propolis containing polyphenols, as a human oral nutritional supplement or as a medicament for preventing and/or limiting the side effects of chemotherapy.

10 Claims, No Drawings

USE OF PROPOLIS FOR COMBATING THE SIDE EFFECTS OF CHEMOTHERAPY

FIELD OF THE INVENTION

This invention relates to preventing and combating the side effects of chemotherapy.

BACKGROUND OF THE INVENTION

Chemotherapy is one of the primary treatments of cancer. It involves an aggressive treatment that makes it possible to attack cancer cells disseminated in the body. However, the attack on cancer cells is not sufficiently targeted and very often leads to unpleasant and negative side effects for the patient, such as a reduction in red blood cells, white blood cells, and platelets, nausea and vomiting, a significant state of fatigue, loss of hair and nails, etc.

It is therefore necessary to find an effective solution that can prevent and limit as much as possible the side effects that ensue from treatments by chemotherapy. Currently, there is not a satisfactory solution. In the case of too significant a reduction of red blood cells, oncologists have to slow down the chemotherapy protocol initially provided in order to allow the body time to re-synthesize its red blood cells or they have to accelerate this synthesis by injecting a growth factor, EPO, which has the drawback of promoting the growth of cancer cells as well.

BRIEF SUMMARY OF THE INVENTION

The objective of the invention is to propose a solution that, on the one hand, prepares the body and in particular the healthy cells to be attacked by the chemotherapy agent and at best to withstand it, to limit as much as possible the side effects that ensue from it, and, on the other hand, not to interfere with the effectiveness of the chemotherapy agent.

To respond to this, the invention proposes using a composition that comprises at least one extract of propolis that contains polyphenols.

In particular, the object of the invention is a composition that comprises at least one propolis extract that contains polyphenols, for its application as a health product, in particular as a human oral nutritional supplement or as a medication for preventing and/or limiting the side effects of chemotherapy. Preferably, the composition is a Dietary Food for Special Medical Purposes (FSMP).

Propolis is a product that is produced by bees from resinous, gummy, and balsamic substances, collected on the buds of certain trees and shrubs, with which they incorporate salivary secretions therein.

Surprisingly enough, according to the invention, propolis has good effectiveness for preventing and/or limiting the side effects of chemotherapy.

Advantageously, the administration to a patient undergoing chemotherapy of a composition that comprises at least one propolis extract that contains polyphenols makes it possible to preserve the patient's quality of life.

DETAILED DESCRIPTION OF THE INVENTION

The invention is now described in detail.

The object of the invention is therefore a composition that comprises at least one propolis extract that contains polyphenols for its use as a health product, in particular as a human oral nutritional supplement or as a medication, for preventing and/or limiting the side effects of chemotherapy.

Propolis extract is defined as any collected propolis that is transformed by an extraction process that makes it possible to remove the impurities that are present in the crude extract and/or to concentrate the propolis in one or more of its components.

The propolis extract can come in any form. Preferably, it comes in the form of a powder.

The useful propolis extract according to the invention is a propolis extract that comprises at least 20% polyphenols by weight of dry material of the extract.

The propolis that is used can be of any well-identified botanical origin. For example, it can be poplar propolis or *Baccharis* propolis (Brazilian green propolis), in particular *Baccharis dracunculifolia*.

Preferably, the composition comprises a poplar propolis extract and/or a *Baccharis* propolis extract.

When the propolis extract is a poplar propolis extract, it preferably comprises at least 30% polyphenols by weight of dry material of the extract.

The extract that is present in the composition can be obtained by a process that comprises the following stages:
  Extraction of propolis,
  Concentration.

The extract can then be reconcentrated and finally transformed.

The different stages of the process should be carried out without destroying the active ingredients and without using solvents.

According to a particularly suitable embodiment, the extract that is used according to the invention can be obtained by a process that comprises the following stages:
  Maceration of crude propolis in an alcohol solution, and
  Concentration by evaporation.

The extract can then be transformed into powder.

The propolis extract that is obtained is incorporated into a composition.

The composition that comprises the propolis extract is used as a human oral nutritional supplement or as a medication.

Preferably, the composition according to the invention is a nutritional supplement, in particular a Dietary Food for Special Medical Purposes (FSMP).

The composition according to the invention, in addition to the propolis extract, can contain proteins, glucids, lipids, vitamins, and/or minerals, added in supplements. Preferably, these molecules are added according to the regulation in force on the FSMPs.

The composition can also contain excipients known by one skilled in the art, such as kaolin or Fibregum® or other texturing, coating and gastro-resistant agents that are known in the pharmaceutical field.

According to a suitable embodiment, the composition comes in the form of a micro-encapsulated powder.

The composition according to the invention, when it is an oral nutritional supplement, is administered in addition to and/or as a substitute for meals.

In a preferred manner, the daily dose of composition comprises between 600 and 1,200 mg of propolis extract by weight of dry material. Preferably, the daily dose is divided into 2 or 3 servings.

The composition according to the invention that comprises at least one propolis extract that contains polyphenols is used for its application for preventing and/or limiting the side effects of chemotherapy.

In particular, the composition according to the invention can be used for protecting against and/or limiting the reduction of white blood cells, red blood cells, and blood platelets following injections of chemotherapy agents.

Actually, the injection of chemotherapy agents brings about a reduction of white blood cells, red blood cells, and blood platelets, and the use of a propolis extract that contains polyphenols makes it possible to limit this reduction.

In addition, the composition according to the invention can be used to protect against and/or to limit the free-radical damage caused by chemotherapy agents to organs, in particular to the liver, the kidneys, and/or the heart.

Advantageously, owing to its action in particular on the limitation of the reduction of white blood cells, red blood cells, and blood platelets, and on the limitation of free-radical damage, the composition according to the invention makes it possible to prevent and/or to combat nausea, hair loss, nail loss, states of fatigue and depression in individuals undergoing chemotherapy treatment.

The invention is now illustrated by examples and test results.

Examples of Propolis Extracts

The propolis that is used, in particular poplar propolis, can be obtained by implementing the grid method which makes it possible to obtain propolis with particular characteristics suitable for medical use in comparison to propolis obtained by the scraping method. The grid method makes it possible to obtain propolis with a higher polyphenol level and a reduced percentage of wax.

Preferably, the percentage of wax in the collected propolis is less than 21%, even more preferably less than 17%.

Once the propolis is collected, it is treated by implementing an extraction process comprising the following stages:
 Propolis is mixed in an extractor with alcohol according to a ratio of 1/2.5 to 1/5 (w/v) for a given time period,
 The mixture then undergoes filtration so as to keep in liquid solution only the active ingredients of propolis: the polyphenols,
 A final clarification by gravitational decanting can optionally be carried out if necessary.

This process makes possible the development of a liquid extract that is concentrated in terms of active ingredients.

This liquid extract can then optionally also be concentrated in terms of active ingredients by dealcoholization. A soft extract that is very concentrated in terms of propolis active ingredients is then obtained. This soft extract can be transformed into powder.

Example 1

An example of a propolis extract obtained by implementing this process is a poplar propolis extract in powder form, having at least 30% total polyphenols by weight of dry material.

Among the polyphenols, the extract comprises in particular:
 At least 8% (±0.8%) pinocembrine,
 At least 5% (±0.5%) chrysin,
 At least 4% (±0.4%) galangin, and
 At least 1.8% (±0.18%) CAPE,
with the percentages being given by weight of dry material relative to the total polyphenols that are present in the extract.

Example 2

An example of propolis extract that is obtained by implementing this process is a *Baccharis* propolis extract in powder form, having at least 20% total polyphenols by weight of dry material.

The extract comprises in particular at least 10% (±1%) artepellin C by weight of dry material relative to the total polyphenols that are present in the extract.

Example of Compositions

A useful composition example according to the invention comprises:
 50 to 80% of a propolis extract comprising at least 20% polyphenols, and
 10 to 15% Fibregum, and/or
 10 to 15% silica, and/or
 10 to 15% kaolin, and/or
 10 to 15% of at least one other excipient.

Evaluation of the Effect of Propolis on the Side Effects of Chemotherapy

The objective of the test is to evaluate the effect of the propolis on the cytolysis of progenerating CD34+ stock cells obtained from human bone marrow following the application of chemotherapy treatment (epirubicin and taxotere).

The culture medium that is used is as follows: IMDM, 15 SVF, SCF (50 ng/ml), TPO (50 ng/ml), FK (50 ng/ml).

The test protocol is described below.

On D3: thawing and seeding with 50,000 cells/ml in a flask (75 cm$^3$)

On D0: marking and seeding with 6,000 cells/well in a 96-well plate

Between D0 and D4:
 Treatment of cells with a propolis extract (Example 1) between D0 and D3 with the following doses: 0, 0.5, 1, 4, 10 and 20 µg/ml
 Treatment of cells with chemotherapy agents (epirubicin at $4.74.10^6$ M and taxotere $2.80.10^6$ M) between D1 and D3

On D5: Marking with 5 nM of SYTOX green, and measurement of cytolysis.

The obtained results that are presented in the table below provide the percentage of CD34+ progenerating stock cells that is cytolyzed on D5.

| Propolis µg/ml | Taxotere | Epirubicin |
| --- | --- | --- |
| 0 (Control) | 65.47 | 53.93 |
| 0.5 | 62.50 | 44.77 |
| 1 | 55.40 | 32.30 |
| 5 | 45.03 | 28.07 |
| 10 | 46.33 | 29.83 |
| 20 | 43.40 | 42.57 |

These results show that a propolis extract that is concentrated in polyphenols has a cytoprotective effect with regard to the cytotoxic effects of chemotherapy agents such as epirubicin and taxotere on hematopoietic progenerating lines.

The invention claimed is:

1. A method for preventing and/or limiting the side effects of chemotherapy comprising administering to a subject in need thereof an effective amount of a composition comprising at least one poplar propolis extract that comprises at least 20% by weight of dry material,
  wherein the extract comprises in particular
    at least 8% (±0.8%) pinocembrine,
    at least 5% (±0.5%) chrysin,
    at least 4% (±0.4%) galangin, and
    at least 1.8% (±0.18%) CAPE,
with the percentages being given by weight of dry material relative to the total polyphenols that are present in the extract; and
  wherein the daily dose of the composition comprises between 600 and 1,200 mg of propolis extract by weight of dry material.

2. The method according to claim 1, wherein the composition is a human oral nutritional supplement or is a medication.

3. The method according to claim 1, wherein the composition limits and/or protects the side effects of chemotherapy by limiting and/or protecting against the reduction of white blood cells, red blood cells, and blood platelets following injections of chemotherapy agents.

4. The method according to claim 1, wherein the composition limits and/or protects the side effects of chemotherapy by protecting against and/or limiting the free-radical damage caused by the chemotherapy agents to organs.

5. The method according to claim 1, wherein the composition limits and/or protects the side effects of chemotherapy by protecting against and/or limiting the free-radical damage caused by chemotherapy agents to the liver, the kidneys and/or the heart.

6. The method according to claim 1, wherein the composition limits and/or protects the side effects of chemotherapy by preventing and/or combating nausea, hair loss, nail loss, states of fatigue and depression in individuals undergoing chemotherapy treatment.

7. The method according to claim 1, wherein the at least one propolis extract is a poplar propolis extract that comprises 30% polyphenols by weight of dry material.

8. The method according to claim 1, wherein the composition further comprises proteins, glucids, lipids, vitamins, and/or minerals.

9. The method according to claim 1, wherein the composition is powder.

10. The method according to claim 1, wherein the composition is administered in addition to and/or as a substitute for meals.

* * * * *